(12) United States Patent
Weber et al.

(10) Patent No.: US 10,150,000 B2
(45) Date of Patent: Dec. 11, 2018

(54) LOCKING DEVICE FOR RECUMBENT STEPPER

(71) Applicant: NuStep, Inc., Ann Arbor, MI (US)

(72) Inventors: Matthew P. Weber, Brighton, MI (US); Neil M. Cole, Dexter, MI (US); Daniel C. Shnidman, Ann Arbor, MI (US); Robert A. Law, Ypsilanti, MI (US); Douglas R. Hennigar, Ann Arbor, MI (US); Walter N. Cole, Livonia, MI (US)

(73) Assignee: NUSTEP, INC., Ann Arbor, MI (US)

( * ) Notice: Subject to any disclaimer, the term of this patent is extended or adjusted under 35 U.S.C. 154(b) by 0 days.

(21) Appl. No.: 15/691,907

(22) Filed: Aug. 31, 2017

(65) Prior Publication Data

US 2018/0028859 A1 Feb. 1, 2018

Related U.S. Application Data (63) Continuation of application No. 14/603,830, filed on Jan. 23, 2015, now Pat. No. 9,757,612.

(60) Provisional application No. 61/931,099, filed on Jan. 24, 2014, provisional application No. 61/952,529, filed on Mar. 13, 2014.

(51) Int. Cl.
| | |
|---|---|
| *A63B 22/00* | (2006.01) |
| *A63B 22/06* | (2006.01) |
| *A63B 21/00* | (2006.01) |
| *A63B 21/005* | (2006.01) |
| *A63B 21/22* | (2006.01) |

(52) U.S. Cl.
CPC ...... *A63B 22/0664* (2013.01); *A63B 22/0056* (2013.01); *A63B 21/0051* (2013.01); *A63B 21/00069* (2013.01); *A63B 21/00076* (2013.01); *A63B 21/225* (2013.01); *A63B 22/001* (2013.01); *A63B 2208/0238* (2013.01); *A63B 2220/17* (2013.01); *A63B 2220/20* (2013.01); *A63B 2220/51* (2013.01); *A63B 2230/06* (2013.01)

(58) Field of Classification Search
CPC ............ A63B 22/0056; A63B 22/0058; A63B 22/06–22/0694
See application file for complete search history.

(56) References Cited

U.S. PATENT DOCUMENTS

| | | | | |
|---|---|---|---|---|
| 6,042,517 A | * | 3/2000 | Gunther | A63B 21/0051 188/161 |
| 2004/0043873 A1 | * | 3/2004 | Wilkinson | A63B 22/0005 482/54 |

* cited by examiner

*Primary Examiner* — Loan H Thanh
*Assistant Examiner* — Rae Fischer
(74) *Attorney, Agent, or Firm* — Brinks Gilson & Lione (57) ABSTRACT

A locking device for an exercise system may include a locking member having a contact portion and configured to move between a first position and a second position. When in the first position, the contact portion of the locking member is not in contact with the resistance mechanism of the exercise system, thereby allowing movement of the at least one moveable assembly. When in the second position, the contact portion of the locking member is in contact with the resistance mechanism of the exercise system, thereby preventing movement of the at least one moveable assembly. The device may also include an electrical actuating device having an actuator for selectively engaging the locking device and moving the locking device between a first position and a second position.

13 Claims, 14 Drawing Sheets

LOCKING DEVICE FOR RECUMBENT STEPPER

CROSS REFERENCE TO RELATED APPLICATIONS

This application is a continuation-in-part application of U.S. patent application Ser. No. 14/603,830, which claimed priority to U.S. Provisional Patent Application 61/931,099 filed on Jan. 24, 2014 and U.S. Provisional Patent Application 61/952,529 filed on Mar. 13, 2014, all of which are hereby incorporated by reference in their entirety.

BACKGROUND

1. Field of the Invention

The invention claimed in this application relates to devices for locking the movement of a movable assembly and more particularly to locking devices for locking a movable assembly for an exercise machine.

2. Description of Related Art

Exercise machines, such as cardiovascular exercise machines, generally have a plurality of different movable assemblies. These moveable assemblies can include right and left handle bars and/or right and left leg assemblies that when actuated by the hands or feet provide a form of resistance. This resistance to the movement can provide both a resistance type of strength training as well as cardiovascular training for promoting cardiovascular health.

These exercise systems may include recumbent exercise systems, elliptical exercise systems, or any other type of exercise system that involves the movement of a moveable assembly. Elliptical exercise systems require that the moveable assemblies have pre-defined path or paths and distance of travel, wherein the moveable assembly must be moved in a certain way and certain distance so as to complete the predefined elliptical path. Recumbent steppers are generally more advanced in that they allow movement of the moveable assembly along a pre-defined path, but the distance travelled along the path may vary. For example, in a recumbent system, the user of the recumbent system can push or pull the handle bars and/or pedals a small distance if he or she chooses to do so. This can be advantageous when the user of the recumbent system has limited ability to move the moveable assemblies.

No matter what type of exercise system is utilized, there may be situations that require the use of locking the moveable assemblies in place. For example, it may be advisable to lock the moveable assemblies when the user of the exercise machine is either mounting or dismounting the exercise machine. By so doing, this can prevent potential of injury wherein the user of the exercise machine places an inappropriate amount of weight on one of the moveable assemblies and the moveable assembly moves because it is not locked, causing surprise and possible injury to the user.

Prior art locking systems generally include a pin locking system. In this type of system, a pin is inserted into a hole or recess. The insertion of this pin is such that the pin physically prevents the movement of the moveable assembly. The pin may be placed through the moveable assembly or through a brake mechanism that is in mechanical communication with the moveable assembly. While the system is effective, the number of positions available to lock the moveable assemblies is limited in that there must be a pre-defined hole recess for the pin to be inserted through. Additionally, these systems do not allow movement of the moveable assemblies even when a significant amount of force is applied to these moveable assemblies. This can be problematic in that the moveable assembly will be damaged if too much force is applied to the moveable assembly when the pin is placed in the hole or recess.

SUMMARY

A locking device for an exercise system may include a locking member having a contact portion and configured to move between a first position and a second position. When in the first position, the contact portion of the locking member is not in contact with the resistance mechanism of the exercise system, thereby allowing movement of the at least one moveable assembly. When in the second position, the contact portion of the locking member is in contact with the resistance mechanism of the exercise system, thereby preventing movement of the at least one moveable assembly. The device may also include an electrical actuating device having an actuator for selectively engaging the locking device and moving the locking device between a first position and a second position.

Further objects, features and advantages of this invention will become readily apparent to persons skilled in the art after a review of the following description, with reference to the drawings and claims that are appended to and form a part of this specification.

DETAILED DESCRIPTION

Figure 1:
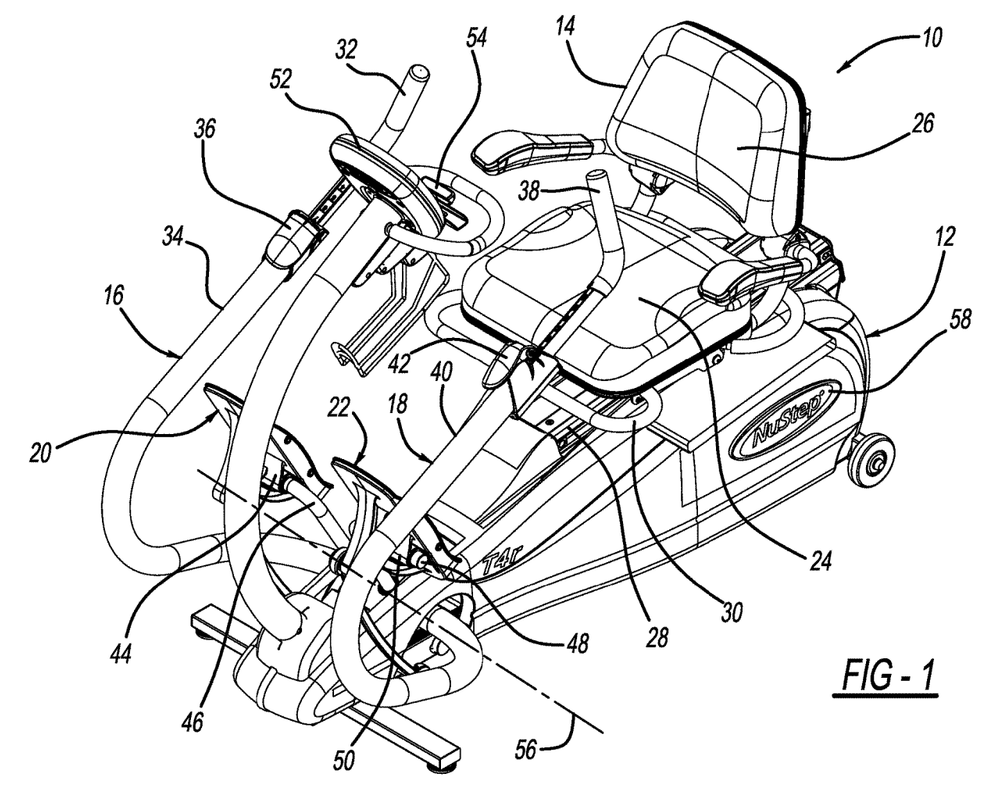
FIG. 1 illustrates an exercise system having a locking device for locking the movement of movable apparatuses of the exercise system.

Referring to FIG. 1, an exercise system 10 is shown. Here, the exercise system 10 is a recumbent stepper 12. Of course, it should be understood that the exercise system 10 may be any one of a number of different exercise systems having moveable apparatuses, such as elliptical exercise systems, or any other type of exercise system that has a moveable apparatus. Additionally, the recumbent stepper 12 is shown and described in U.S. Pat. No. 6,361,479 which is hereby incorporated by reference in its entirety.

As to its primary components, the recumbent stepper 12 includes a seating system 14, a first upper moveable assembly 16, a second upper moveable assembly 18, a first lower moveable assembly 20, and a second lower moveable assembly 22. The seating system 14 may have a base support 24 for supporting the lower part of a user and a back support 26 for supporting the back of the user. The seating system 14 may be moveable along a track 28 that is caused by actuating a handle 30.

The first upper moveable assembly 16 and the second upper moveable assembly 18 are both similar and are essentially a mirror image of each other. The first upper moveable assembly 16 includes a handle bar 32 that is connected to an arm 34. The handle bar 32 may be adjusted so as to lengthen or shorten itself by actuating a locking lever 36. As to the second upper moveable assembly 18, this assembly 18 also includes a handle bar 38 and an arm 40 that also allows the adjustment of the handle bar 38 through the use of another locking lever 42.

Like the upper assemblies 16 and 18, the first and second lower assemblies 20 and 22 are both substantially similar but are generally mirror images of each other. The first lower moveable assembly includes a pedal 44 that has connected to an arm 46. The pedal 44 is generally adjustable. Likewise, the second lower moveable assembly 22 includes a pedal 48 that is adjustably connected to an arm 50.

The recumbent system 12 also includes an information center 52 that provides information to the user of the recumbent stepper 12. Information to the user could include a number of repetitions, distance, resistance, heart rate, or other exercise related information. Located adjacent to the information system 52 may also be an actuator 54. The actuator 54 serves a purpose of allowing one to lock the movement of the moveable apparatuses 16, 18, 20, and 22. More information relating to the locking system and the actuator 54 will be provided later in this description.

In this recumbent system 12, the moveable apparatuses 16, 18, 20, and 22 all rotate about a central axis 56. As stated before, the exercise system 10 is a recumbent system 12 so it allows minimal movement of the movable apparatuses 16, 18, 20, and 22 about the central axis 56. Additionally, the moveable apparatuses 16, 18, 20, and 22 may also move in a contralateral motion. Moreover, that is to say when the first upper moveable apparatus 16 moves away from the seating system 14, the second upper moveable apparatus 18 will move toward the seating system 14. Similarly, when the first lower moveable apparatus 20 is moved away from the seating system 14, the second lower moveable apparatus 20 will move towards the seating system 14 and vice versa. Resistance is provided to the moveable apparatuses 16, 18, 20, and 22 by a resistance mechanism located within a housing 58.

Figure 2:
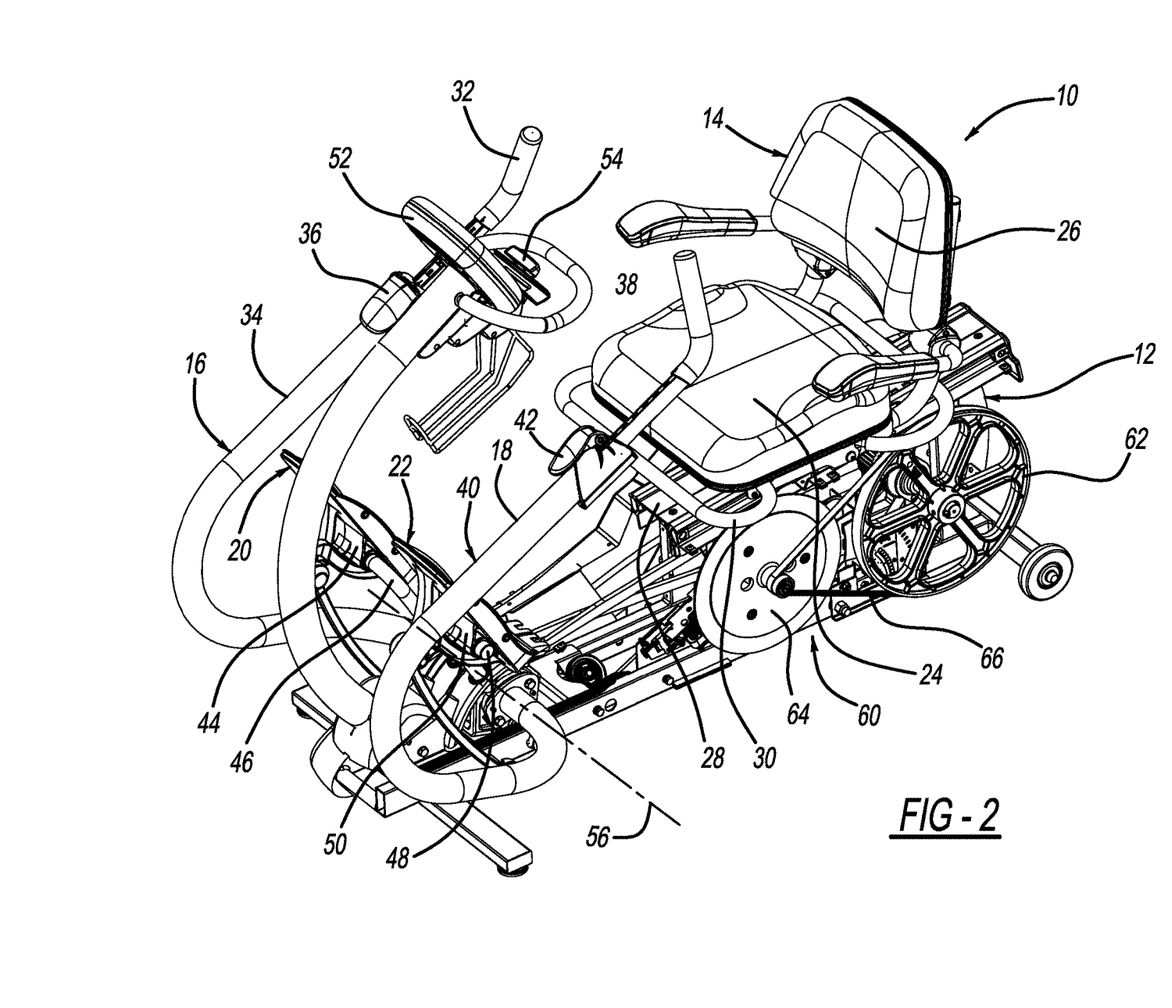
FIG. 2 illustrates the exercise system of FIG. 1 with the housing removed.

Referring to FIG. 2, a view of the recumbent system 12 is shown without the housing 58 so as to provide a more clear view of the resistance mechanism 60. The moveable apparatuses 16, 18, 20, and 22 each move a series of belts and pulleys that eventually move a flywheel 62. The flywheel 62 is in communication with a brake 64 via a belt 66. The brake 64 provides resistance to the moveable apparatuses 16, 18, 20, and 22 by providing resistance via an eddy-current type mechanism. Adjustment of this eddy-current type mechanism allows the resistance provided to the moveable apparatuses 16, 18, 20, and 22 to be varied. This allows the user of the exercise system 10 to be able to adjust the resistance so as to change the intensity of their workout.

Figure 3:
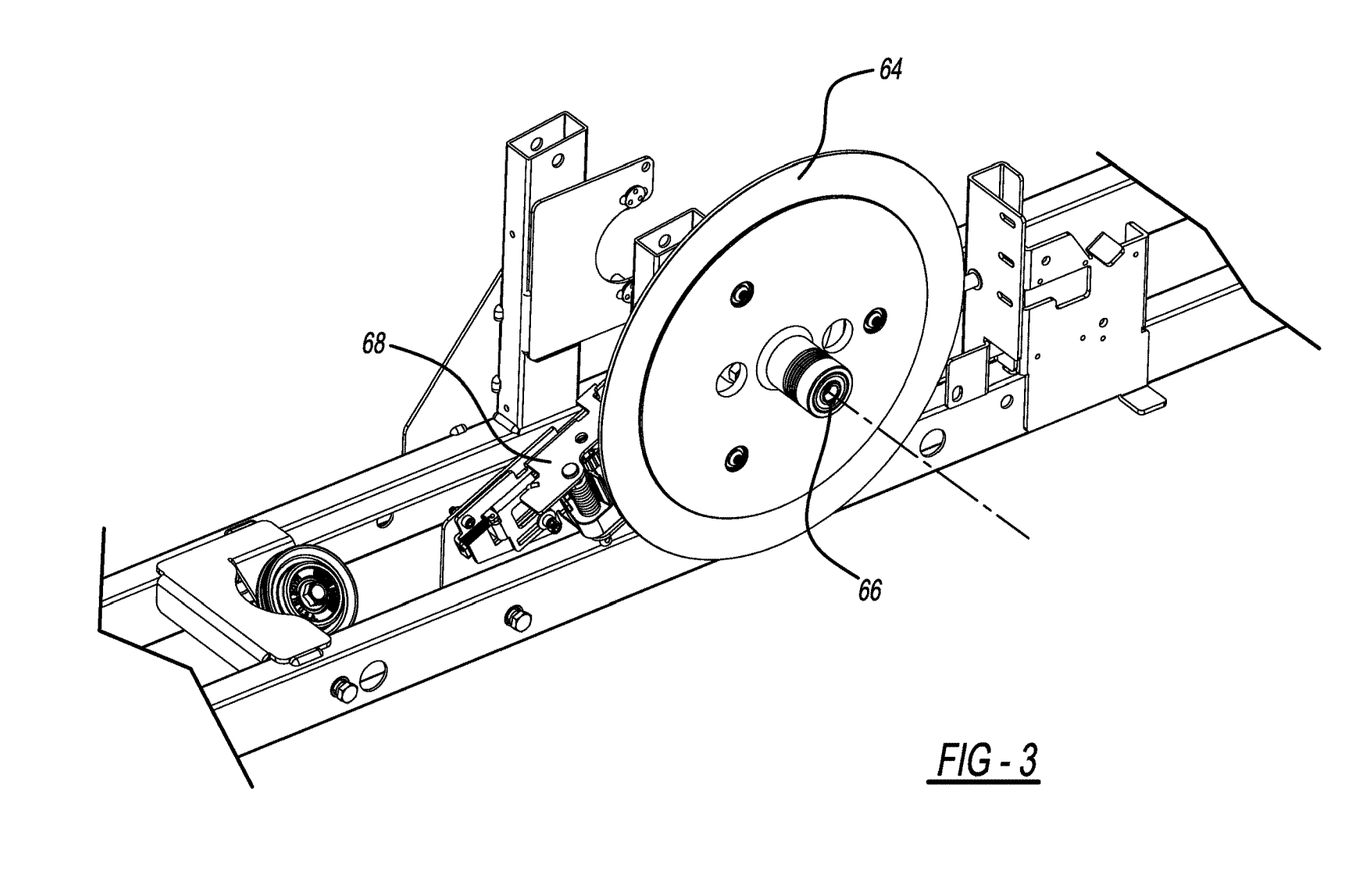
FIG. 3 illustrates a more detailed view of a brake of the exercise system of FIG. 1.

Referring to FIG. 3, a more detailed view of the brake 64 is shown. In an effort to better show the nearby components of the brake 64, many components have been removed from this view. Including the housing 58, flywheel 62, belt 66, seating system 14 and track 30. Here, the brake 64 is a disk whose resistance around the rotation of an axis 66 is determined by adjustment of an eddy-current device. If one were to prevent the movement of the disk 64, the moveable apparatuses 16, 18, 20, and 22 would be prevented to move because they are connected to the brake disk 64 via a series of belts and the flywheel 62, such that if the disk 64 does not move, the moveable apparatuses 16, 18, 20, and 22 will not be able to move either. In order to prevent the movement of the disk 64, a locking device 68 is utilized.

Figure 4:
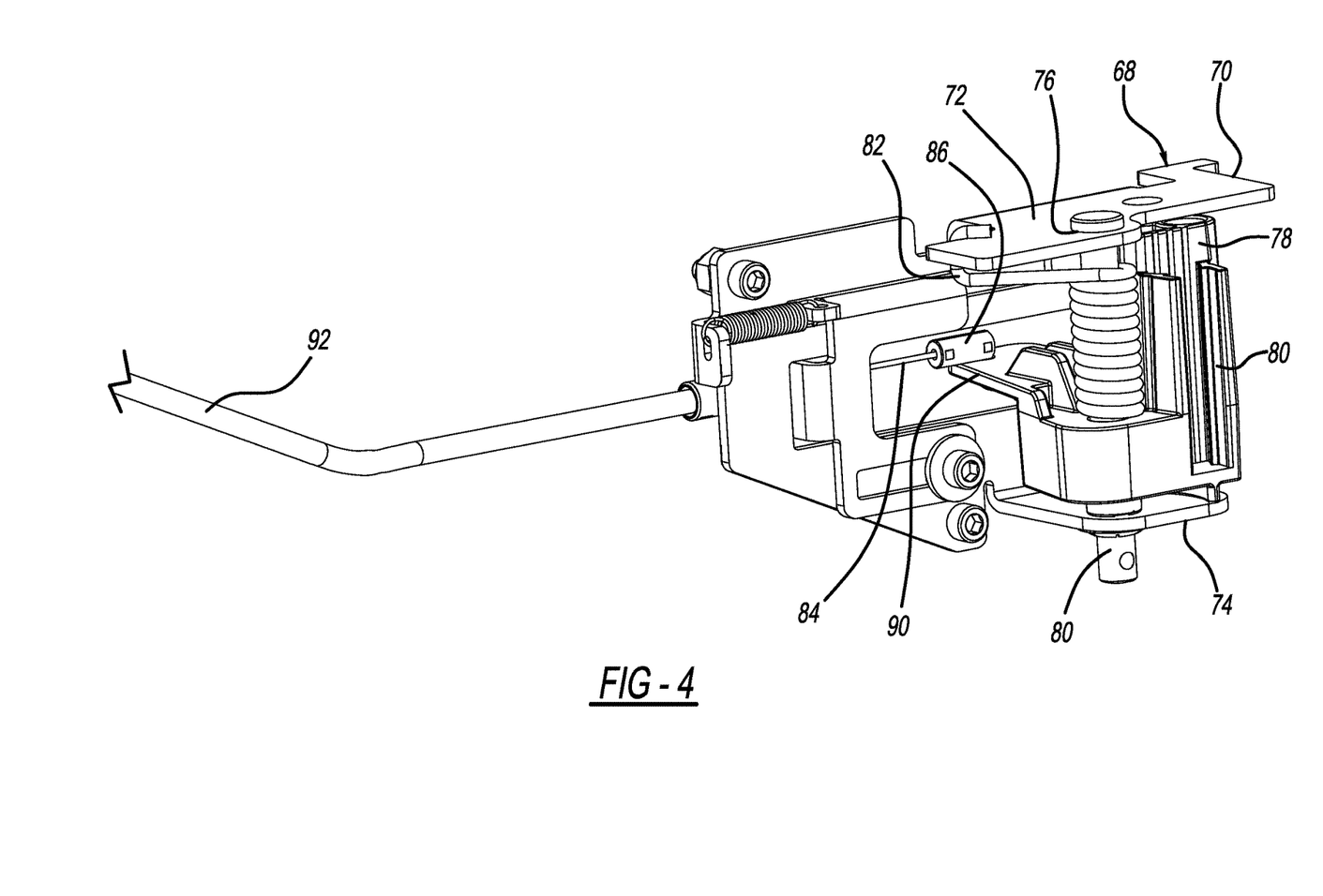
FIG. 4 illustrates a more detailed view of the locking device of the exercise system of FIG. 1.

Referring to FIG. 4, a more detailed view of the locking device 68 is shown. Here, the locking device has a housing 70 that contains an upper portion 72 and a lower portion 74. The upper portion 74 has a hole 76 that extends through the upper portion 72 and through the lower portion 74. The locking device 68 also includes a contact portion 78 that is located between both the upper portion 72 and the lower portion 74. The contact portion 78 rotates about an axis defined by the hole 76. When the pin is inserted thusly, the contact portion 78 can rotate about the axis defined by the pin 80. The contact portion 78 also includes an engagement portion 80 that may be made out of a softer material, such as rubber or Kevlar. A spring 82 biases the contact portion 78 towards the disk 64. As such, without any additional biasing, the contact portion 78 is always biased towards the disk 64, thereby preventing the movement of the disk 64. As such, in its normal state, the contact portion 78 is biased toward the disk 64 thereby preventing movement of the disk 64 and the moveable assemblies 16, 18, 20, and 22.

In order to allow movement of the disk 64 and therefore movement of the moveable assembly 16, 18, 20, and 22, the contact portion 78 is biased against the spring 82 by a cord 84, that may be a wire, with an end 86 that is connected to a flange 90 that is part of the contact portion 78. Depending on how much length of the cord 84 is provided, the wire can pull on the flange 90 such that the contact portion 78 is drawn away from the disk 64 allowing the movement of the disk 64 and the mobile apparatuses 16, 18, 20, and 22. This cord 84 extends away from the locking device 68 through a tubing 92.

Figure 5:
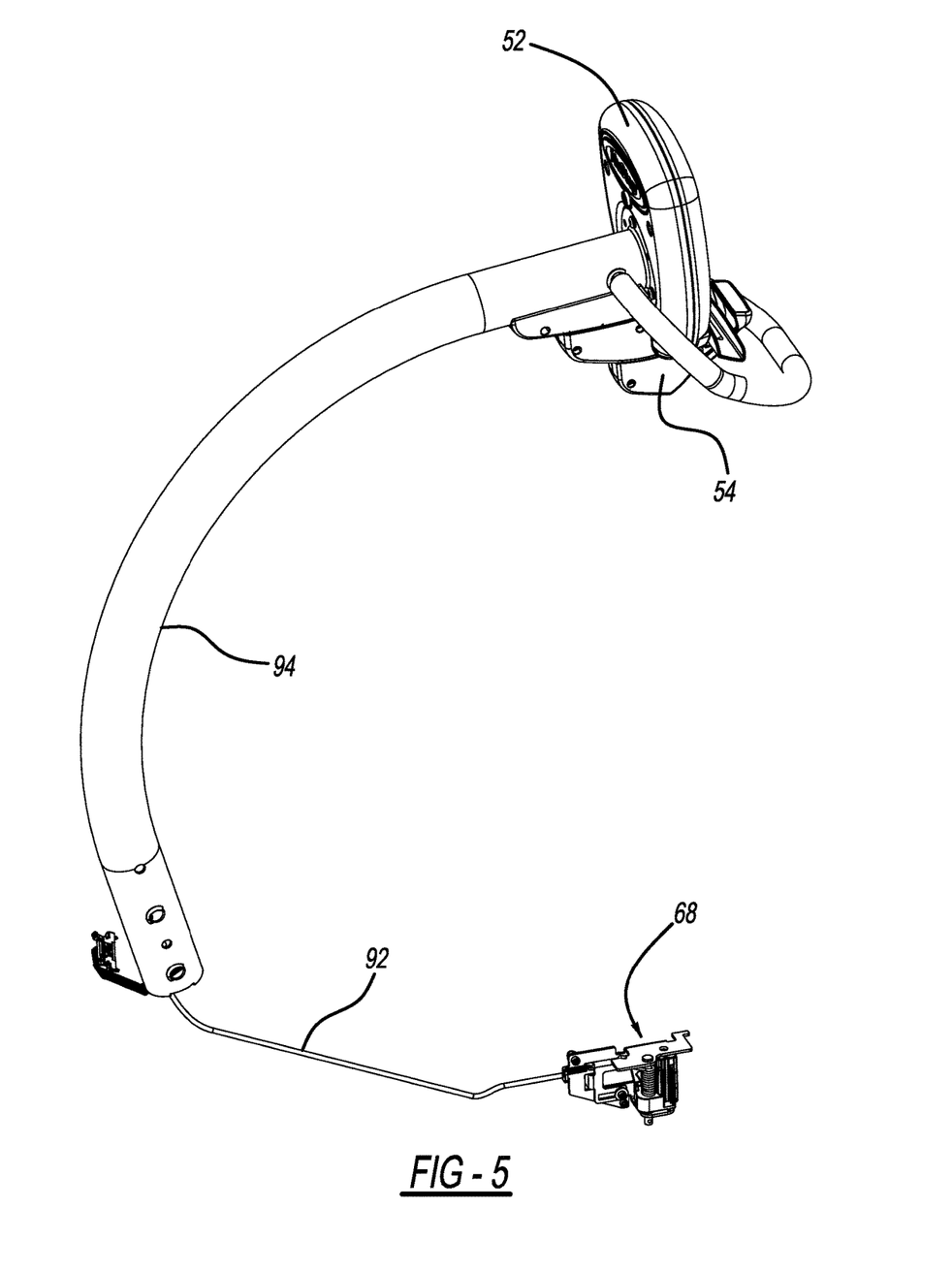
FIG. 5 illustrates another detailed view of the locking device of the exercise system of FIG. 1.

Referring to FIG. 5, illustrated is a locking device 68 as well as the tubing 92 that contains the cord 84. The tubing 92 extends away from a locking device 68 and up a neck 94 of the recumbent stepper to the control center 52. As stated previously, the control center 52 has an actuator 54 for actuating the locking device 68. The cord 84 extends through the tubing 92 which as well as the tubing 92 extends up the neck 94 to the actuator 54.

Figure 6:
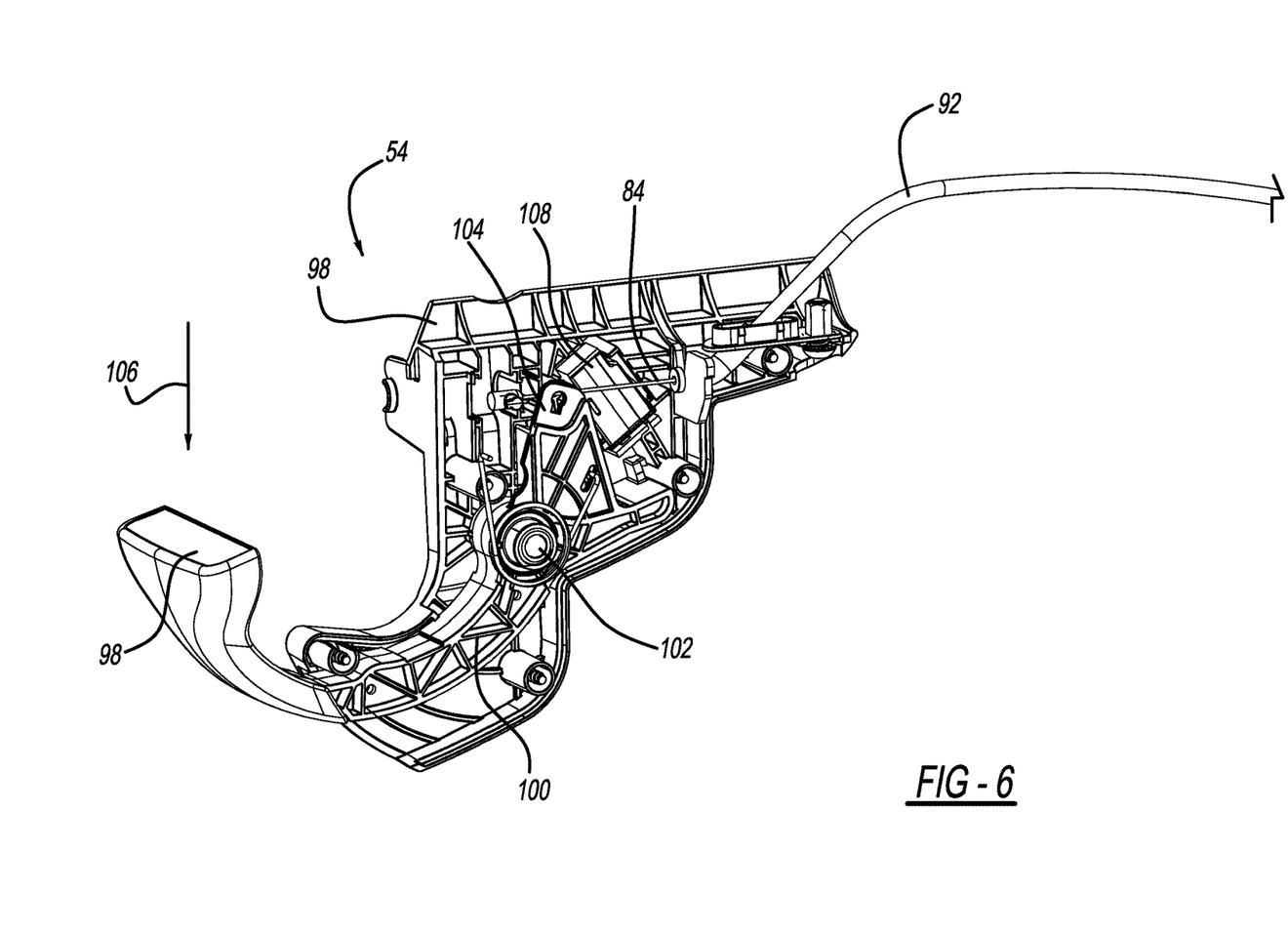
FIG. 6 illustrates an actuator for actuating the locking device of the exercise system of FIG. 1.

Referring to FIG. 6, a more detailed view of the actuator 54 is shown. Here, the actuator 54 has portions of a housing 96 of the actuator 54 removed so as details of the actuator 54 can be shown. The actuator 54 includes a button 98 that can be in one of two positions. As stated before, the housing 92 containing the cord 84 is provided from the locking device 68 to the actuator 54. The button 98 is connected to an arm 100 that rotates about an axis 102. A top portion 104 of the arm 100 is connected to another end of the cord 84. Therefore, when the button 98 is pressed in a downward motion as indicated by the arrow 106, the wire 84 will be pulled which will in turn unlock the locking device 68. The button 98 has one of two positions that are dictated by a push pull mechanism 108.

The push pull mechanism 108 is essentially a two position switch. When in the first position, the push pull mechanism limits the movement of the arm 100 such that the cord 84 is preventing the locking device from locking the disk 64. Essentially, the button 98 has two positions. In one position, the button 98 pulls the cord 84 which then actuates the locking device 68 allowing the disk 64 to rotate freely. In the other position, the button allows the locking device 68 to come into contact with the disk 64 preventing the movement thereof. The locking device 68 has the distinct advantage in that the locking device has an infinite number of lockable positions. This allows the user of the exercise system 26 to lock the moveable apparatuses 16, 18, 20, and 22 in any one of a number of different positions.

Referring back to FIG. 4, the locking device 68 also has the advantage in that if the cord 84 breaks, the contact device 78 will place the contact surface 80 in contact with the disk 64 because the spring 82 biases the contact mechanism 78 towards the disk 64. This provides a safety feature in that if there is a malfunction in the locking device, thus preventing movement of the disk 64 and the moveable apparatuses 16, 18, 20, and 22. In addition, because the locking device 68 contacts the disk 64 using a contact portion 80, the locking device 68 can be configured to allow movement of the moveable apparatuses 16, 18, 20, and 22 when an amount of force that is applied to at least one of the moveable apparatuses 16, 18, 20, and 22 exceeds a predefined threshold. This threshold can be adjusted by increasing or decreasing the bias provided by the spring 82.

Figure 7:
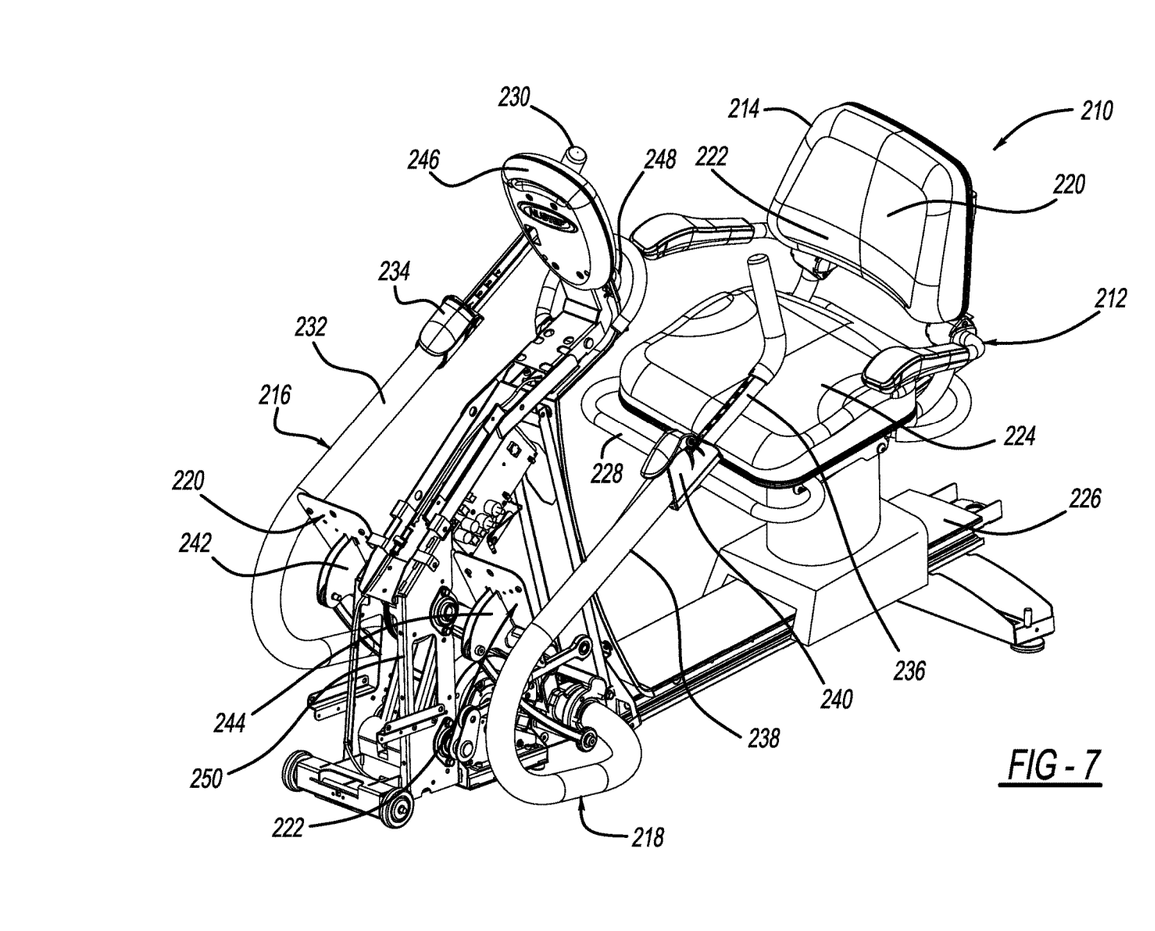
FIG. 7 illustrates another embodiment of an exercise system having a locking device for locking the movement of movable apparatuses of the exercise system.

Referring to FIG. 7, another embodiment of the locking device is shown. Here, an exercise system 210 that maybe a recumbent stepper 212. As its basic components, the recumbent stepper 212 includes a seating system 214, a first upper moveable apparatus 216, a second upper moveable apparatus 218, a first lower moveable apparatus 220, and a second lower moveable apparatus 222. It should be understood that this type of recumbent stepper 212 is further disclosed in U.S. Pat. No. 7,775,942 which is herein incorporated by reference in its entirety.

Like before, the seating system 214 may have a seat 220 that has a seat back 222 and a base seating surface 224. The seating system 214 may be mounted to a track 226 that allows the seating system 214 to slide along the track 226. Generally, the seating system 214 can be engages so as to slide around the track via a handle 228.

The first upper moveable apparatus 216 may include a handlebar 230 that is adjustable along its length into an arm portion 232. The adjustment of the handlebar 230 along the arm portion 232 occurs by actuating a locking device 234. Similarly, the second upper moveable apparatus 218 also includes a handlebar 236 that extends into an arm 238. A locking device 240 allows the handlebar 236 to extend along the length of the arm 238 and lock the handle bar into place.

The first lower moveable apparatus 220 includes an adjustable pedal 242, while the second lower moveable apparatus 222 also includes an adjustable pedal 244. Of course, it should be understood that the moveable apparatuses 216, 218, 220, and 222 could take any one of a number of different forms and/or may not be adjustable in nature.

Also shown is a command center 246 that has a display that provides information to the user of the recumbent stepper 212. Like before, this information could include resistance, repetitions, distance, heart rate, or any other information that would be relevant to a user of the recumbent stepper 212. Directly below the command center 246 is an actuator 248 that allows or locks the movement of the moveable apparatuses 216, 218, 220, and 222. Additional details regarding the actuator 248 and the system for locking the moveable apparatuses 216, 218, 220, and 222 will be given later in this description. Furthermore, a housing 250 surrounds a resistance mechanism that provides resistance to the moveable apparatuses 216, 218, 220, and 222.

Figure 8:
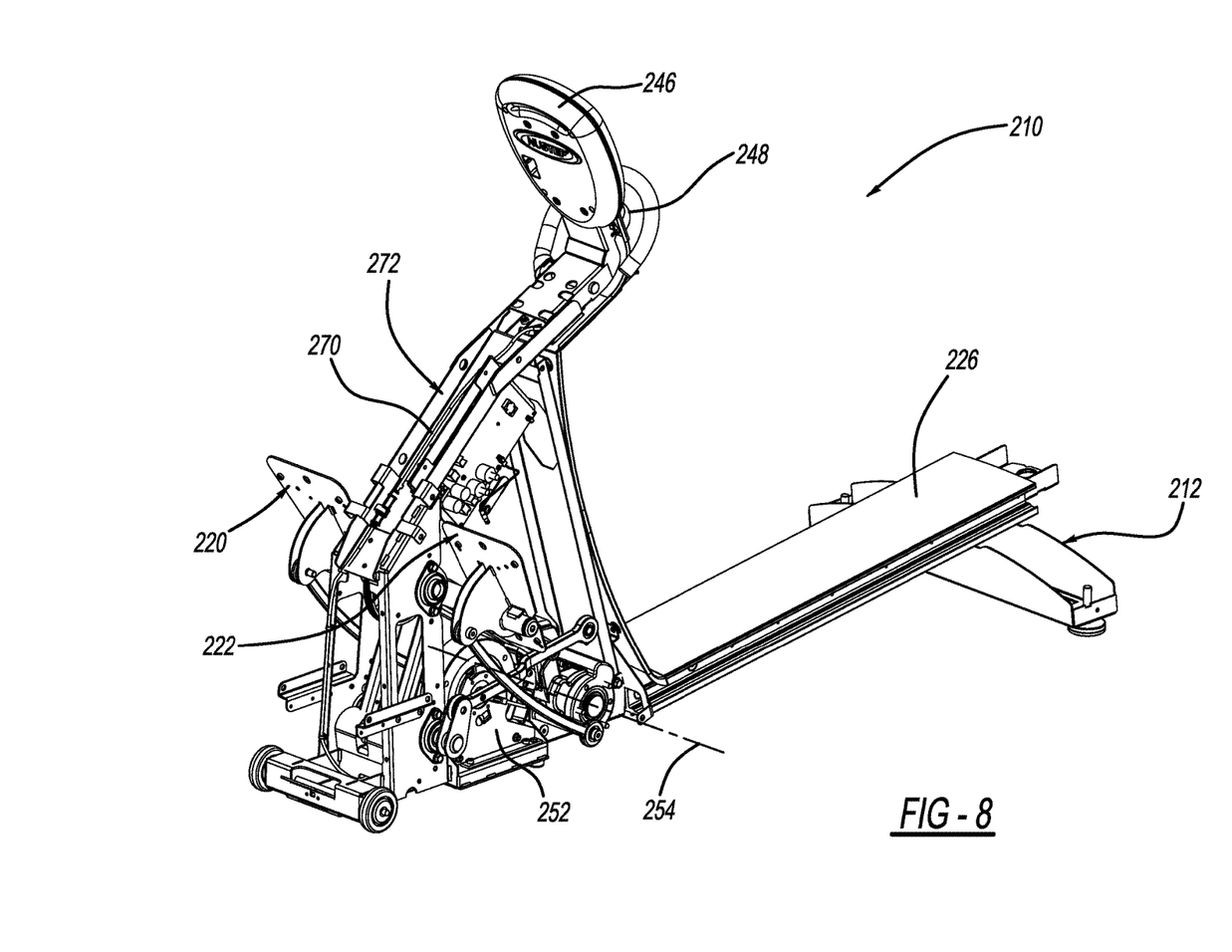
FIG. 8 illustrates the exercise system of FIG. 7 with the housing removed.

Referring to FIG. 8, a more simplified view of the exercise system 210 is shown. In this view, the recumbent stepper 212 has the housing 250 removed as well as the seating system 214 and the upper moveable apparatuses 216 and 218. Located generally below and between the lower moveable apparatuses 220 and 222 is a resistance mechanism 252. The resistance mechanism is in mechanical communication with the moveable apparatuses 216, 218, 220, and 222 through a variety of belts and clutches. Generally, the resistance mechanism 252 provides resistance to the moveable apparatuses 216, 218, 220, and 222 via a mechanical system. Generally, the moveable apparatuses 216, 218, 220, and 222 rotate about a central axis 254 in a contralateral type manner.

Figure 9:
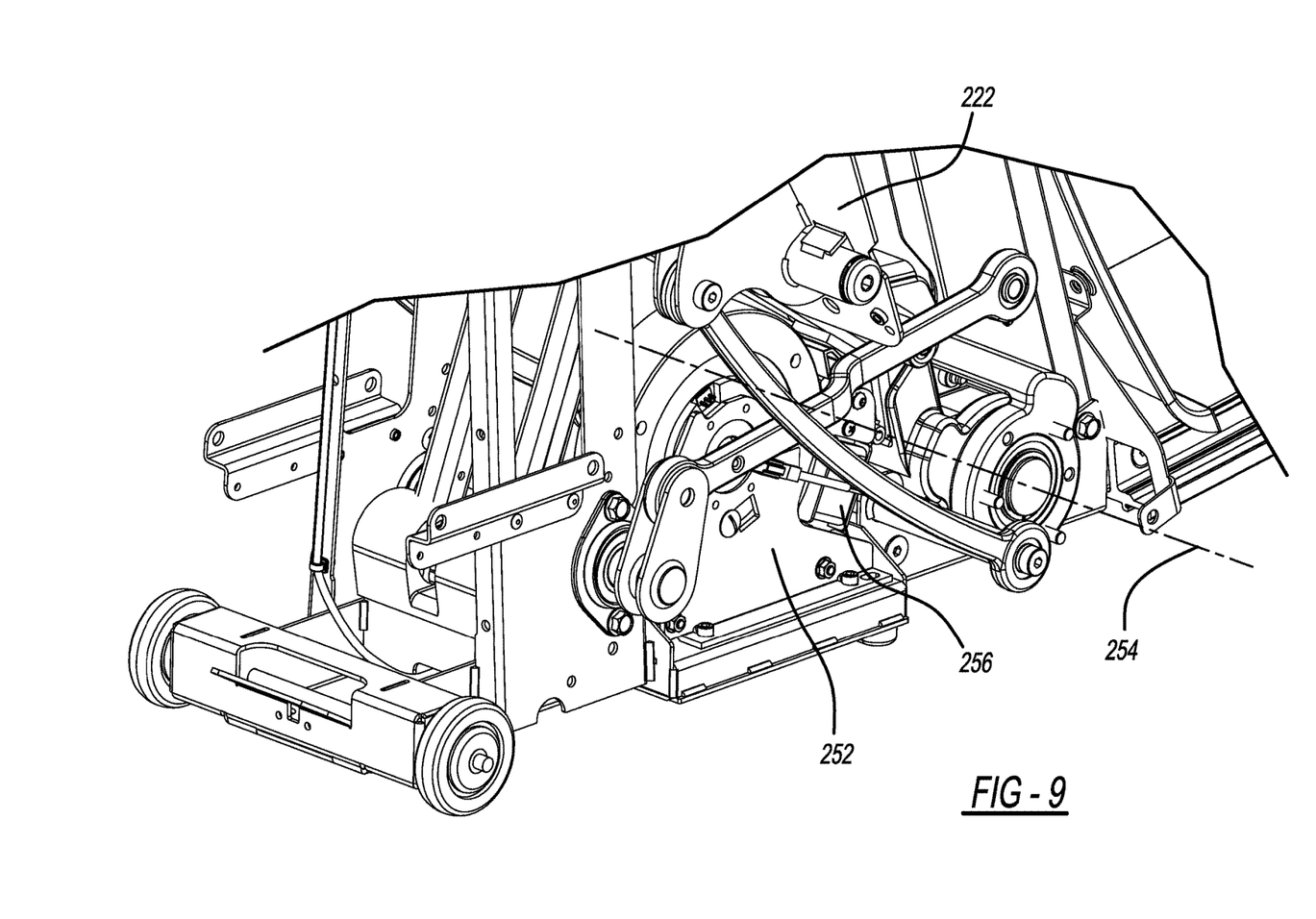
FIG. 9 illustrates a more detailed view of the resistance mechanism of the exercise system of FIG. 7.

Referring to FIG. 9, a more detailed view of the resistance mechanism 252 is shown. This resistance mechanism can be adjusted by the central information center 246. Also shown is a locking device 256. The locking device 256 restricts the movement of the resistance mechanism 252 when actuated by the actuating device 248. When properly actuated, the resistance mechanism 256 will prevent rotation of the resistance mechanism 252 which thereby prevents the movement of the moveable apparatuses 216, 218, 220, and 222.

Figure 10:
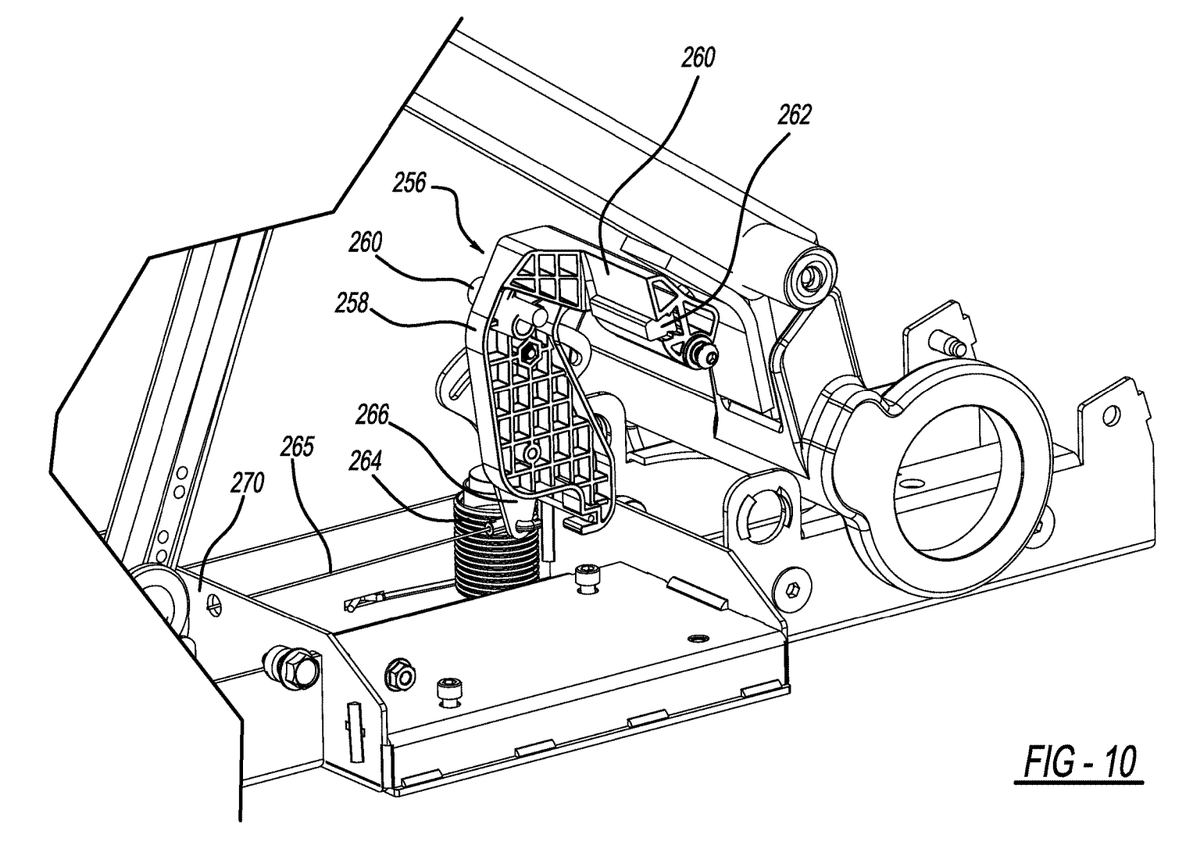
FIGS. 10 and 11 illustrates a more detailed view of the locking device of the exercise system of FIG. 7.
Figure 11:
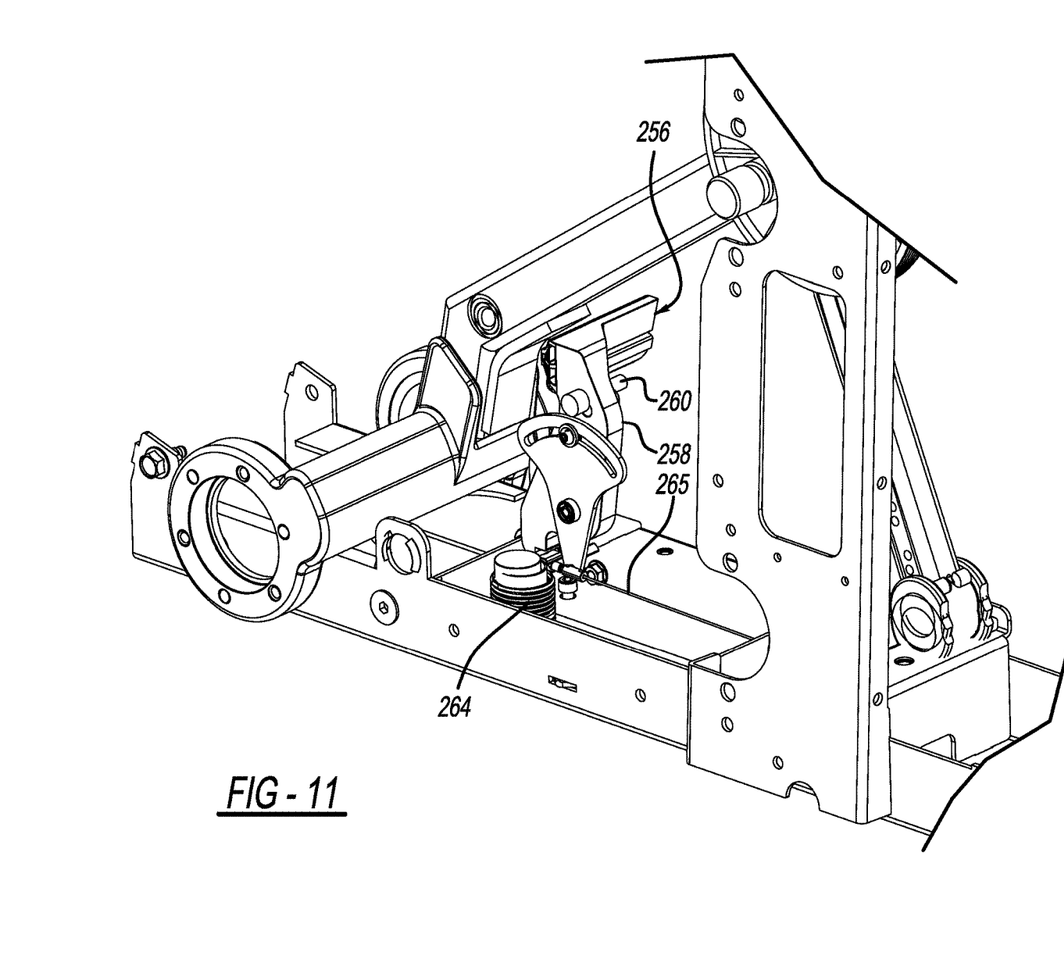

Referring to FIGS. 10 and 11 a close up view of the locking mechanism 256 is shown. In these figures, the resistance mechanism 252 has been removed so the locking device 256 can be more clearly shown. Here, the locking device 256 includes a first portion 258 that generally extends upward from the surface in which the exercise system 210 is located. Extending perpendicularly from the first portion 258 is a second portion 260 that extends generally perpendicular from the first portion 258. Attached to the second portion 260 is a contact portion 262 that may be made out of a flexible material. The contact portion 262 will make contact with the resistance mechanism 252.

A spring 264 biases the first portion 258 around an axel 260. This bias presses the contact portion 262 into the resistance mechanism 252 which prevents the resistance mechanism and therefore the moveable apparatuses 216, 218, 220, and 222 from moving. In order to allow movement of the resistance mechanism 252, a wire 265 is attached to flange 266 which is in turn attached to the first portion 258 of a locking device 256. When the cord 265 is pulled against the biasing of the spring 264, the contact portion 262 is moved away from the resistance mechanism 252 allowing the resistance mechanism 252 to move freely.

Like the other embodiment, the spring 264 biases the contact member 262 towards the resistance mechanism 252 thereby locking the device when the spring 264 has a free range of movement. The cord 265 extends from the resistance mechanism 256 into a tubing 270. The cord 265 and tubing 270 extend through a neck portion 272 to the command center 246 and the actuator 248. As stated before, the actuator 258 will pull the cord 265 so as to move the locking device 256 from either an unlocked or locked position.

Figure 12:
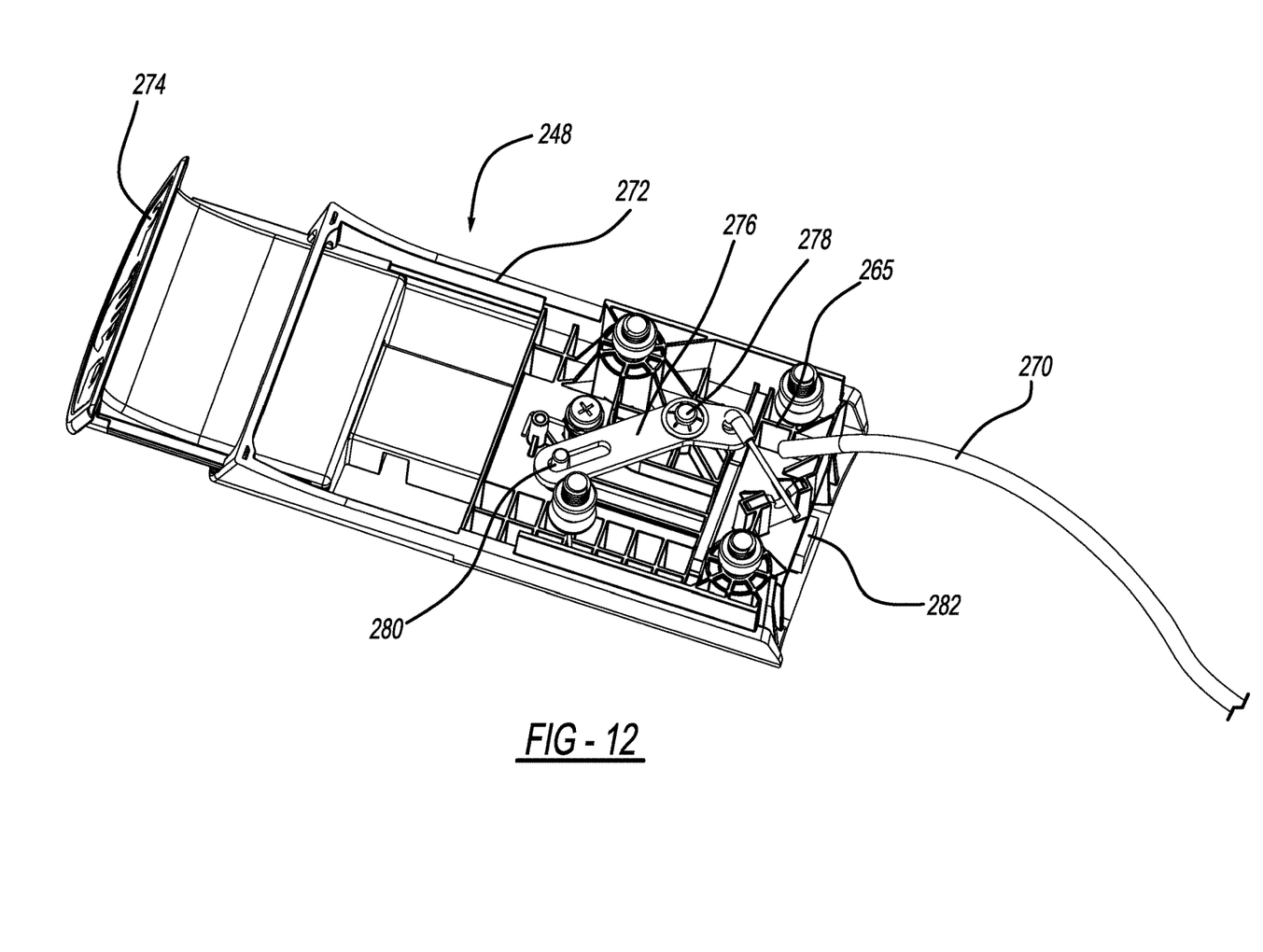
FIG. 12 illustrates an actuator for actuating the locking device of the exercise system of FIG. 7.

Referring to FIG. 12, a more detailed view of the actuator 248 is shown. Here, the actuator 248 includes a housing 272 with the top portion of the housing 272 removed so as to show the inner workings of the actuator 248. The actuator 248 also includes a button 274 that allows the user to actuate the actuator 248. The actuator 248 includes an arm 276 that rotates about a central axis defined by an axel 278. Connected on one end of the arm 276 is the cord 265 while the other end of the arm 276 is connected to a peg 280 that can be moved by the button 274. A push pull button 282 provides one of two positions for the arm 276. In the first position, the arm 276 is placed such that the wire 265 is slightly pulled allowing the resistance mechanism 252 to rotate freely. In a second position, the arm 276 is slightly rotated in a different direction allowing the wire 265 to shorten thereby causing the locking mechanism 256 to prevent movement of the resistance mechanism 252.

Like before, in a situation with a cord 265 breaks or detaches the resistance mechanism 256 is biased by the spring 264 so as to lock the resistance mechanism 252. This, in turn, prevents the movement of the moveable apparatuses 216, 218, 220, and 222. Additionally, this system also has the advantage in that there are an infinite number of lockable positions thereby allowing the user of the exercise machine 210 to lock the moveable apparatuses 216, 218, 220, and 222 in any one of the number of different positions. Further, this system has the advantage of allowing the moveable apparatuses 216, 218, 220, and 222 to move even when locked when a sufficient amount of force is applied to one of the apparatuses, thereby preventing damage to the exercise system 210.

Figure 13:
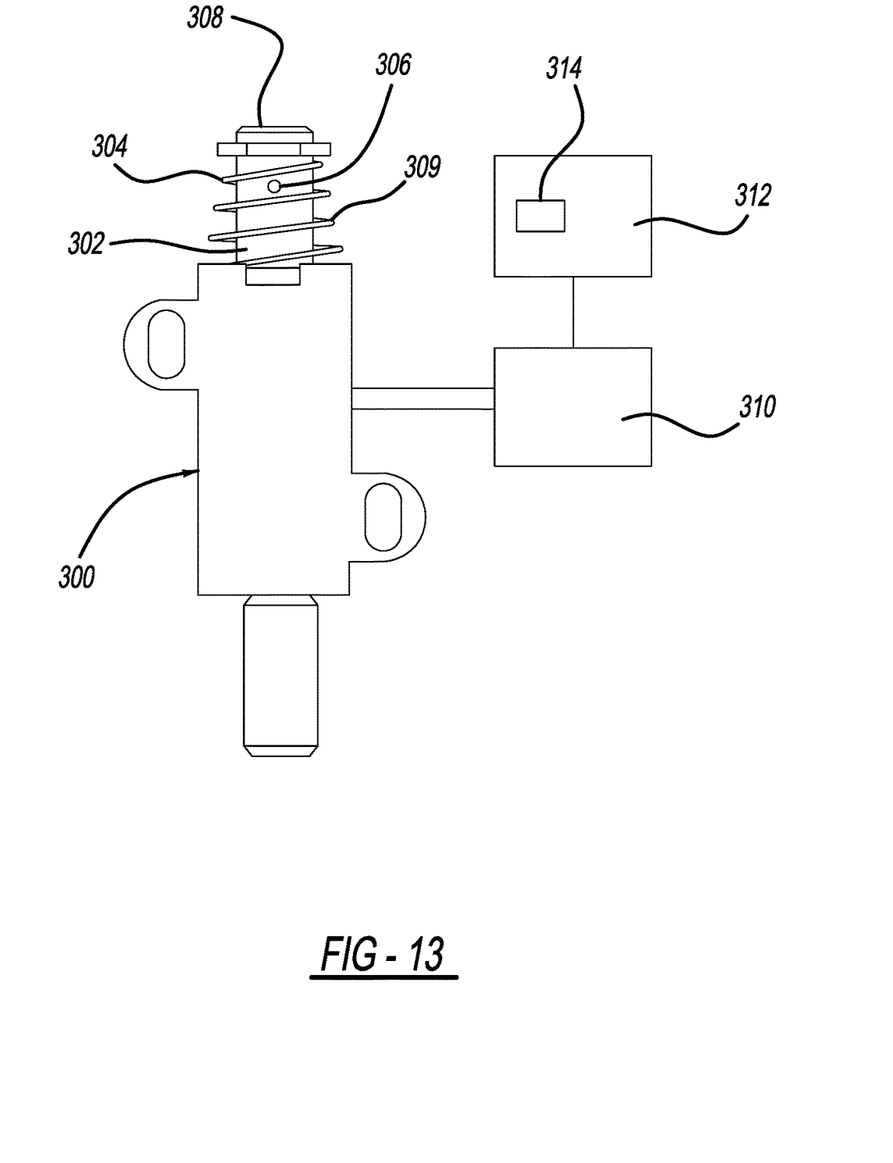
FIG. 13 illustrates an electrical actuating device having an actuator for selectively engaging the locking device and moving the locking device between a first position and a second position and a related control system.
Figure 14:
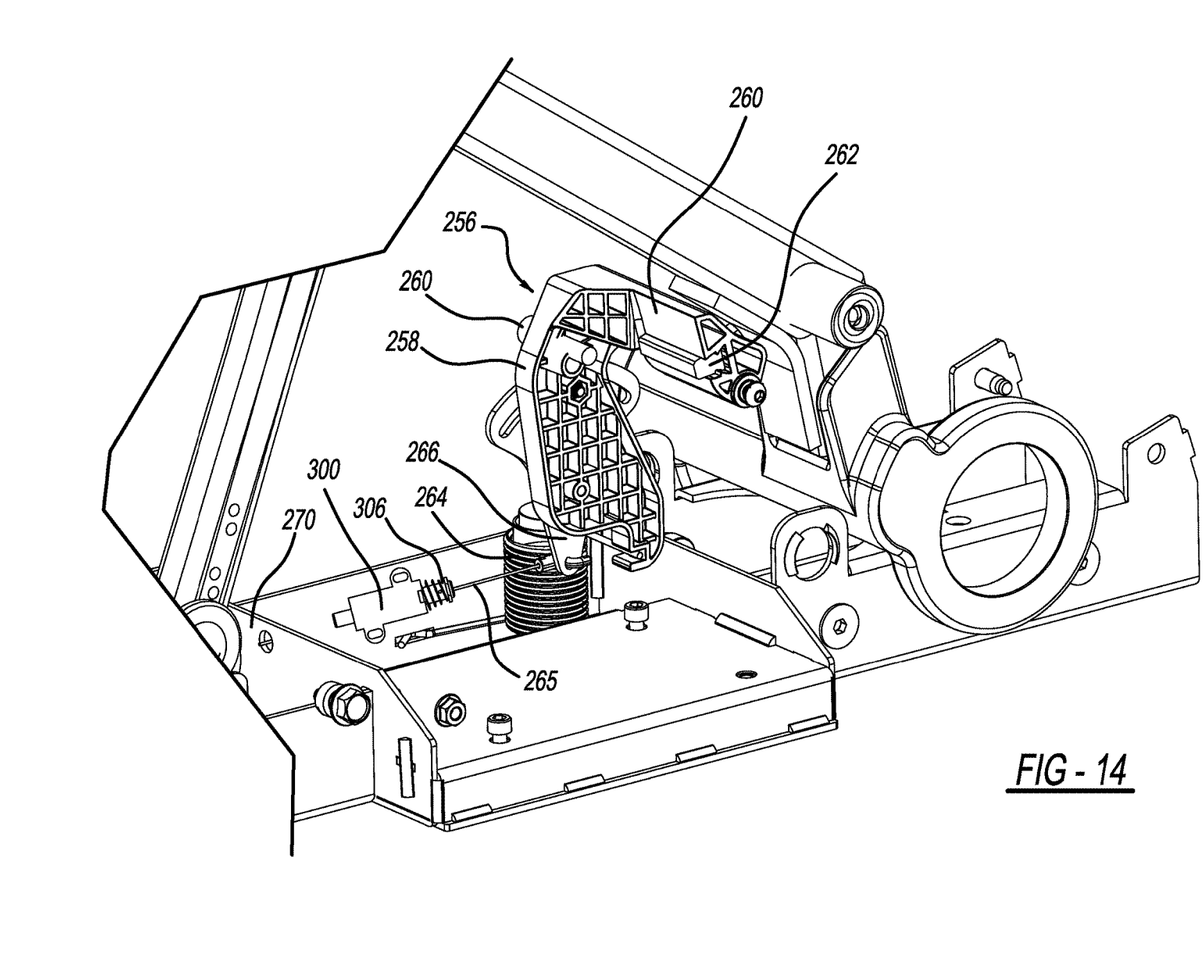
FIG. 14 illustrates a more detailed view of the locking device of the exercise system utilizing the electrical actuating device.

Referring to FIGS. 13 and 14, and electronic actuating device 300 is shown. Instead of utilizing a mechanical actuating device as mentioned in the paragraphs describing FIGS. 1-12, the actuation of the locking device 256 is performed by the electronic actuating device. The electronic actuating device 300 may be an electrical motor or a solenoid, such as a push-pull solenoid. Here, the electronic actuating device 300 is illustrated as a push-pull solenoid. The push-pull solenoid 300 includes an actuator 302 that is capable of moving between at least two positions. The actuator 302 may be biased into one of the positions by the spring 304. As such, when the solenoid 300 is energized, the actuator 302 will press down against the spring 304. When the solenoid 300 is de-energized, the solenoid 300 moves to the position shown in FIG. 13. It is conceivable that the solenoid 300 may not utilize the spring 304 and may instead depend on the biasing force provided by the spring 264. Additionally, it is also conceivable that the spring 264 could be removed and that the solenoid 300 rely entirely on the biasing force provided by the spring 304. Finally, it is also conceivable that the device include and utilize both springs 264 and 304.

In addition, the actuator 302 of the solenoid 300 may include a hole 306 and/or a flat surface 308. The hole 306 could be shaped and placed such that it is capable of interacting with the cord 265. So, for example, based on the energization of the solenoid 300 the cord 265 can be pushed or pulled into one of two positions. As stated in the previous paragraphs, as the cord 265 is tightened or loosened, the locking device 256 can move between one of two positions so as to lock the one or more assemblies of the recumbent stepper in place or allow the free movement of these one or more assemblies.

Alternatively, the flat surface portion 308 may be placed such that it directly engages the locking device 256 so as to push or pull the locking device 256 into a locked position. The solenoid 300 may be controlled by a control system 312 that includes an input 314. The input 314 could be a physical pushbutton or could be a touchscreen found in the command center 246.

The control system 312 may be connected to an energy source 310 that is in turn electrically connected to the solenoid 300. The energy source 310 is capable of providing the appropriate current so as to energize or de-energize the solenoid 300. As stated before, this energization or de-energization of the solenoid 300 functions to move the actuator 302 into one of two positions.

As a person skilled in the art will readily appreciate, the above description is meant as an illustration of implementation of the principles this invention. This description is not intended to limit the scope or application of this invention in that the invention is susceptible to modification, variation and change, without departing from the spirit of this invention, as defined in the following claims.

The invention claimed is:

1. A locking device for an exercise system, the exercise system having at least one moveable assembly in communication with a resistance mechanism, comprising:
   a locking member having a contact portion and configured to move between a first position and a second position;
   wherein, when in the first position, the contact portion of the locking member is not in contact with the resistance mechanism of the exercise system, thereby allowing movement of the at least one moveable assembly;
   wherein, when in the second position, the contact portion of the locking member is in contact with the resistance mechanism of the exercise system, thereby preventing movement of the at least one moveable assembly; and
   an electrical actuating device having an actuator for selectively engaging the locking device and moving the locking device between a first position and a second position.

2. The locking device of claim 1, wherein the electrical actuating device is at least one push-pull solenoid.

3. The locking device of claim 2, wherein the actuator of the push-pull solenoid is configured to move the locking member into the first position when the push-pull solenoid is energized, thereby allowing movement of the at least one moveable assembly.

4. The locking device of claim 3, further comprising a spring, wherein the locking member is biased towards the second position by the spring, wherein when the push-pull solenoid is de-energized.

5. The locking device of claim 1, wherein the electrical actuating device is an electric motor.

6. The locking device of claim 1, further comprising an input device for controlling the electrical actuating device so as to move the locking device between the first position and a second position.

7. The locking device of claim 1, wherein the exercise system is a recumbent stepper.

8. The locking device of claim 7, wherein the recumbent stepper further comprises:
   a frame;
   a left arm assembly and a right arm assembly, the arm assemblies supported by the frame for pivoting movement also about a central pivot axis, the arm assemblies each including an upwardly extending arm lever terminating in a handle;
   a left leg assembly and a right leg assembly, the leg assemblies supported by the frame for pivoting movement about the central pivot axis, the leg assemblies each including an upwardly extending leg lever terminating in a pedal;
   the left leg assembly being connected to the right arm assembly enabling concurrent movement of the two assemblies and defining a first connected assembly, the right leg assembly being connected to the left arm assembly enabling concurrent movement of the two assemblies and defining a second connected assembly; and the resistance mechanism being in mechanical communication with the first and second connected assemblies.

9. The locking device of claim 1, wherein the exercise system is a recumbent cycle.

10. The locking device of claim 1, wherein the resistance mechanism is a magnetic resistance device comprising at least one magnet on a linear actuator, the linear actuator moving the magnet in a linear direction to vary the resistance provided by an eddy current disk, wherein the contact portion of the locking member is in contact with the eddy current disk of the exercise system when the locking device is in the second position, thereby preventing movement of the at least one moveable assembly.

11. The locking device of claim 1, wherein when the contact portion of the locking member is in contact with the resistance mechanism of the exercise system, the locking device engages a predefined portion of the resistance mechanism, thereby providing a finite number of positions for locking the at least one moveable assembly.

12. The locking device of claim 1, wherein when the contact portion of the locking member is in contact with the resistance mechanism of the exercise system, the locking device engages any portion of the resistance mechanism, thereby providing an infinite number of positions for locking the at least one moveable assembly.

13. The locking device of claim 1, wherein when the contact portion of the locking member is in contact with the resistance mechanism of the exercise system, the locking member is configured to allow movement of the at least one moveable assembly when an amount of force that is applied to the at least one moveable assembly exceeds a predefined threshold.

* * * * *